(12) United States Patent
Jackson

(10) Patent No.: US 7,235,105 B2
(45) Date of Patent: *Jun. 26, 2007

(54) THREADED CENTER LINE CAGE WITH WINGED END GAP

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 51 days.

This patent is subject to a terminal disclaimer.

(21) Appl. No.: 10/666,589

(22) Filed: Sep. 18, 2003

(65) Prior Publication Data
US 2005/0065606 A1    Mar. 24, 2005

(51) Int. Cl.
*A61F 2/44* (2006.01)
(52) U.S. Cl. .................................. 623/17.16
(58) Field of Classification Search ........... 606/60, 606/61; 623/11.11, 16.11, 17.11–17.16, 623/23.5
See application file for complete search history.

(56) References Cited

U.S. PATENT DOCUMENTS

| | | | |
|---|---|---|---|
| 4,834,757 A | 5/1989 | Brantigan | |
| 5,458,638 A | 10/1995 | Kuslich et al. | |
| 5,489,308 A | 2/1996 | Kuslich et al. | |
| 5,554,191 A | 9/1996 | Lahille et al. | |
| 5,609,636 A | 3/1997 | Kohrs et al. | |
| 5,645,598 A * | 7/1997 | Brosnahan, III | 606/61 |
| 5,658,337 A | 8/1997 | Kohrs et al. | |
| 5,665,122 A | 9/1997 | Kambin | |
| 5,669,909 A | 9/1997 | Zdeblick et al. | |
| 5,681,135 A | 10/1997 | Simonson | |
| 5,683,394 A * | 11/1997 | Rinner | 606/86 |
| 5,693,100 A | 12/1997 | Pisharodi | |
| 5,716,355 A | 2/1998 | Jackson et al. | |
| 5,782,919 A | 7/1998 | Zdeblick et al. | |
| 5,865,847 A | 2/1999 | Kohrs et al. | |
| 5,904,719 A | 5/1999 | Errico et al. | |
| 5,941,880 A | 8/1999 | Errico et al. | |
| 5,968,098 A | 10/1999 | Winslow | |
| 5,980,522 A | 11/1999 | Koros et al. | |
| 6,117,174 A | 9/2000 | Nolan | |
| 6,120,503 A * | 9/2000 | Michelson | 606/61 |
| 6,123,705 A | 9/2000 | Michelson | |
| 6,129,763 A | 10/2000 | Chauvin et al. | |
| 6,165,219 A | 12/2000 | Kohrs et al. | |
| 6,176,882 B1 | 1/2001 | Biedermann et al. | |
| 6,206,922 B1 | 3/2001 | Zdeblick et al. | |
| 6,217,579 B1 * | 4/2001 | Koros | 606/61 |

(Continued)

FOREIGN PATENT DOCUMENTS

GB     2364643 A  *  2/2002

*Primary Examiner*—Anu Ramana
(74) *Attorney, Agent, or Firm*—John C. McMahon

(57) ABSTRACT

A threaded center line cage assembly includes a cylindrical intervertebral spacer member to which is attached a winged end cap. The spacer member is implanted along a center line or median plane between a pair of adjacent vertebrae to engage inner regions of mutually facing surfaces of the vertebrae. The end cap engages edge regions of the vertebrae to provide lateral support thereto, in cooperation with the spacer member. The spacer member is provided with threads having roots which vary in a conically diminishing manner in a posterior direction and then become constant to form an effectively funnel shaped profile to the thread roots. The funnel shaped profile of the roots tends to promote a desired lordosis between the adjacent vertebrae.

16 Claims, 4 Drawing Sheets

U.S. PATENT DOCUMENTS

| | | |
|---|---|---|
| 6,224,631 B1 | 5/2001 | Kohrs |
| 6,306,170 B2 * | 10/2001 | Ray .................. 623/17.11 |
| 6,436,139 B1 * | 8/2002 | Shapiro et al. ........ 623/17.11 |
| 6,440,170 B1 | 8/2002 | Jackson |
| 6,447,546 B1 * | 9/2002 | Bramlet et al. ........ 623/17.16 |
| 6,579,290 B1 * | 6/2003 | Hardcastle et al. ......... 606/61 |
| 6,613,091 B1 * | 9/2003 | Zdeblick et al. ....... 623/17.16 |
| 6,926,737 B2 * | 8/2005 | Jackson .................. 623/17.16 |

* cited by examiner

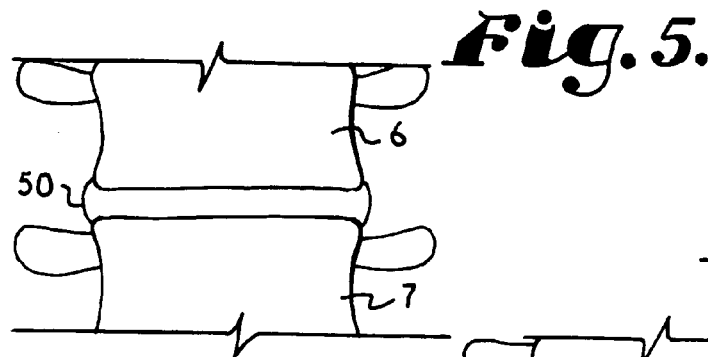
Fig.5.
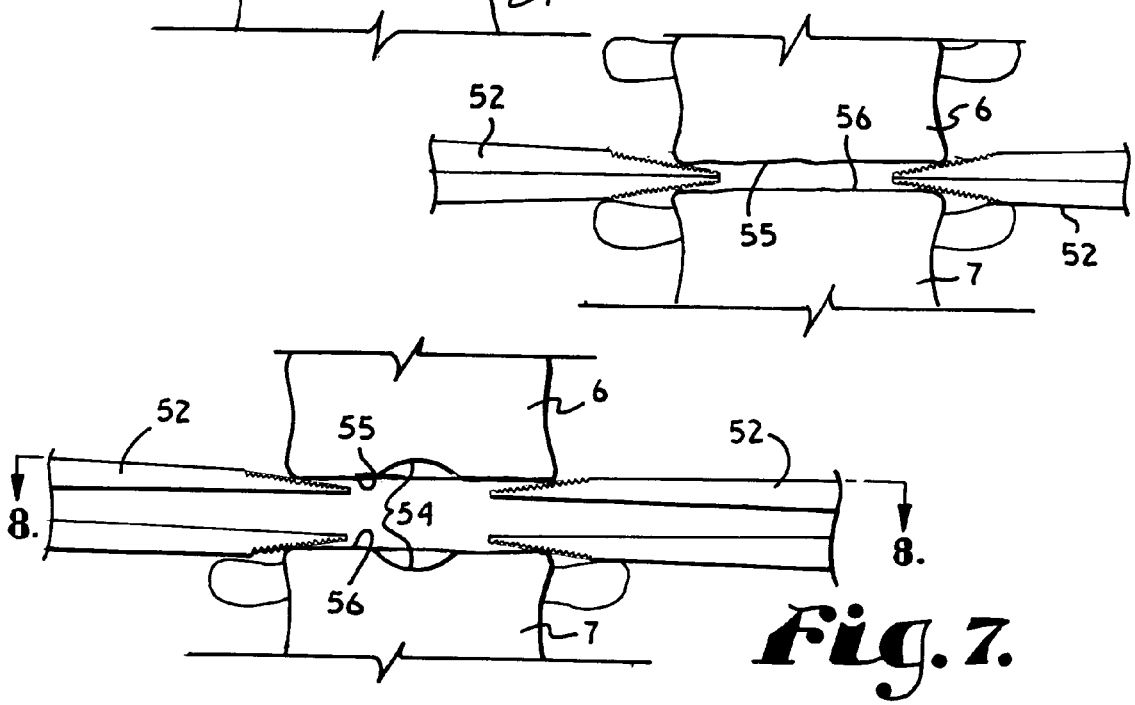
Fig.6.
Fig.7.
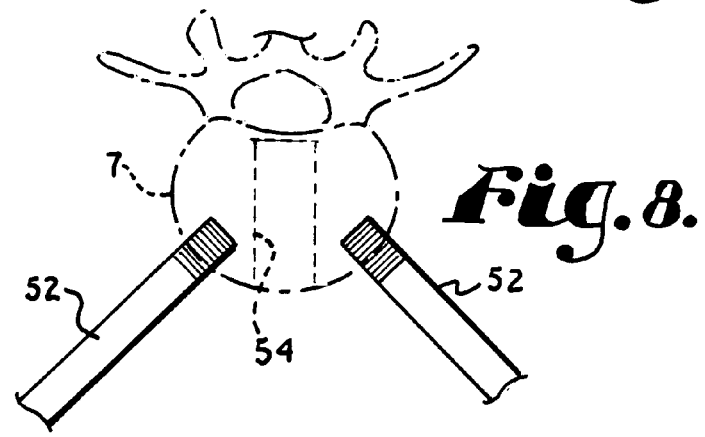
Fig.8.

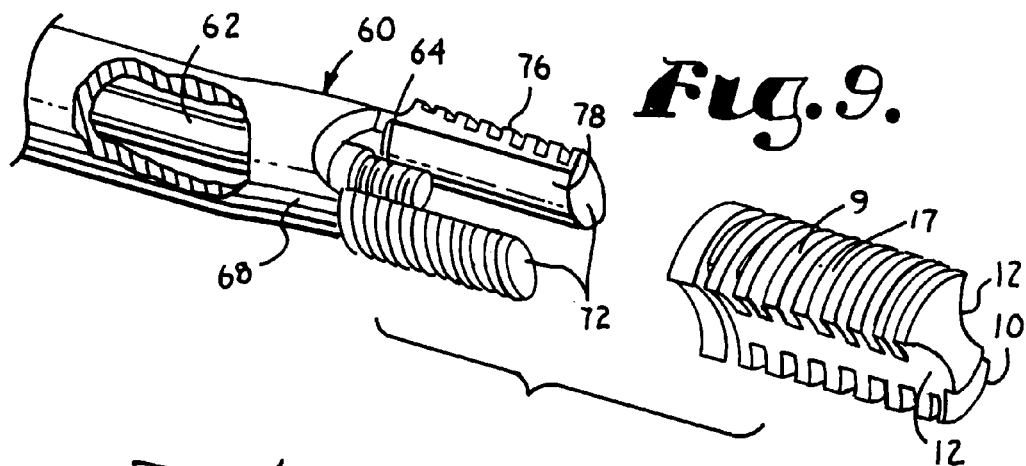
Fig. 9.
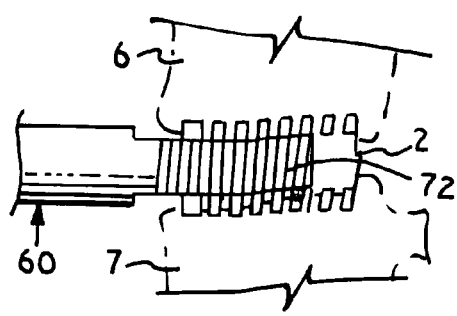
Fig. 11.
Fig. 10.
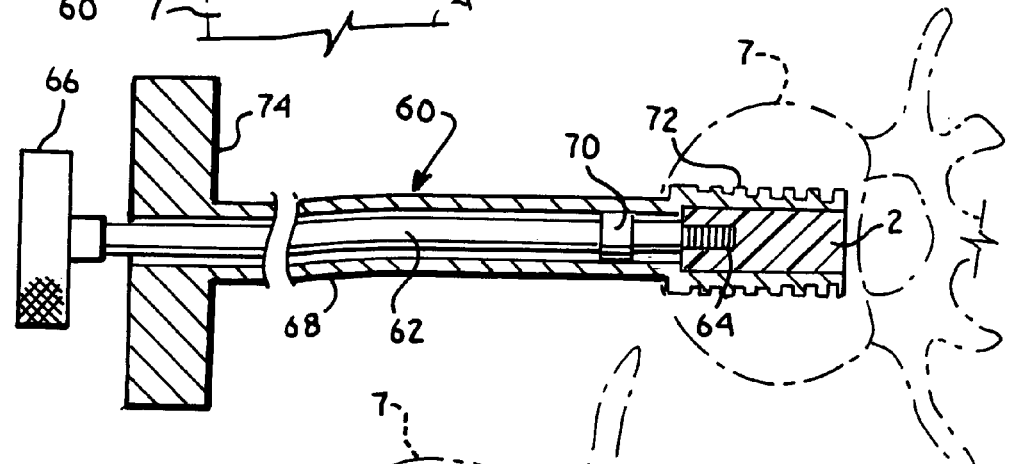
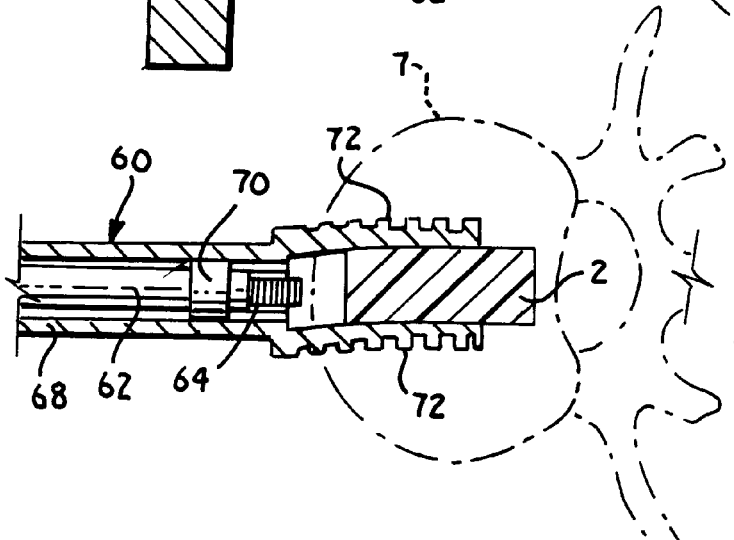
Fig 12.

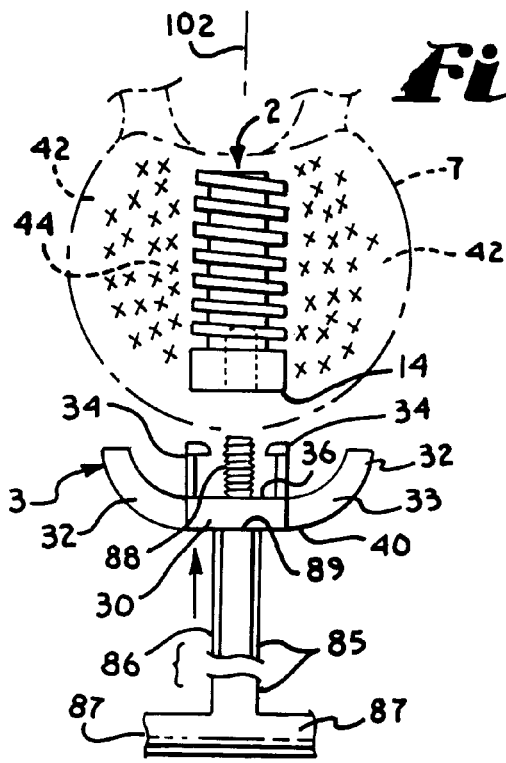
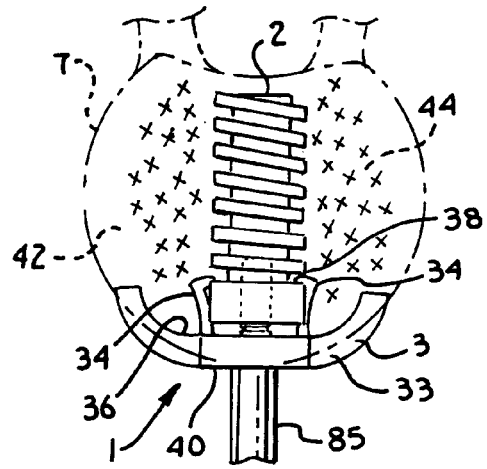
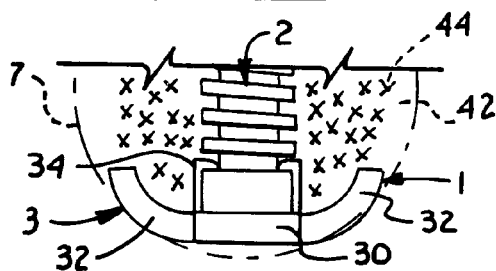
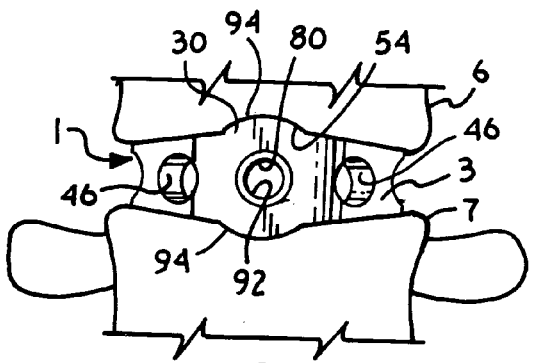
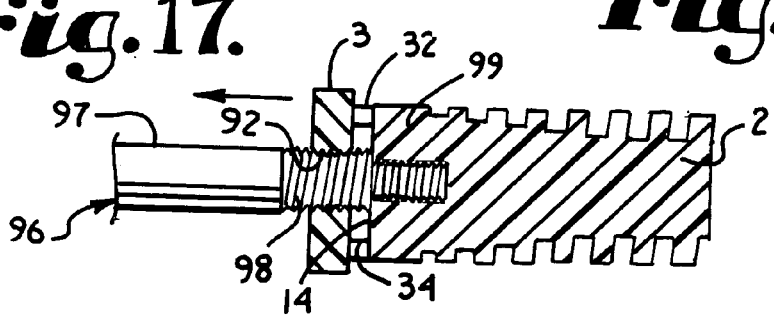

THREADED CENTER LINE CAGE WITH WINGED END GAP

BACKGROUND OF THE INVENTION

The present application is directed to a center line threaded cage with a winged end cap for implantation between a pair of adjacent vertebrae in order to provide spacing, orientation, and support to the vertebrae and to promote fusion between the vertebrae.

In the human spine, the pad or disc between vertebrae is sometimes damaged or deteriorates due to age, disease, injury, or congenital defect. The vertebrae may also become compressed or otherwise damaged. Because of this, surgery is often utilized to place spacers or interbody devices between the vertebrae which provide proper spacing of the vertebrae and which also promote fusion between the vertebrae. When a device of this type is utilized for purposes of promoting fusion, it is often referred to as a fusion cage or an intervertebral fusion device. When utilized to promote fusion, the interbody devices often are windowed and packed with bone fusion material to promote growth of the bone between the vertebrae. Sometimes such material is packed between a pair of devices that are placed in close proximity to one another between the vertebrae to promote growth of bone and, therefore, fusion between the vertebrae.

In the past, interbody devices have typically been either generally rectangular or cylindrical in shape. The cylindrical devices have an advantage that they can be threadably received more or less directly between and into the adjacent vertebrae. For this purpose, the vertebrae are typically first spaced apart, and then a tool is utilized to create a partial bore in each vertebra which with spacing of the vertebrae allows the interbody device to be received between the vertebrae. Because of the natural space between the bones, the interbody device usually engages the bones only along an upper surface and a lower surface thereof. When the cage is of a cylindrical threaded type, the upper and lower surfaces are curved and essentially designed to engage the portion of the vertebrae where bone is unremoved during boring to create an opening for the device.

When interbody devices of this type are used, it is desirable that the device engage as much surface of bone as possible to provide strength and to reduce the likelihood of subsidence of the device into the bone, resulting from contact pressure of the interbody spacer on an intervertebral surface of a vertebra, since part of the bone is spongy by nature, especially near the center. The remainder of the structure mainly functions to support the two engagement surfaces, unless the device is also used as a cage within which to pack bone fusion material. Because it is also desirable in such structures to maintain weight and volume as low as possible, in order to make the device more compatible with the body, it is also desirable to make the entire device as small and lightweight as possible, while maintaining sufficient strength to prevent catastrophic failure.

As noted above, the mutually facing intervertebral surfaces of an adjacent pair of vertebrae have different characteristics over their areas. Central regions of the surfaces are somewhat spongy, such that there is a tendency of the interbody spacers to subside or sink into the vertebrae in the central regions. In contrast, outer or edge regions of the surfaces are more solid and generally harder. When a fusion cage is implanted, particularly a threaded cylindrical cage, it has previously been the practice to implant two such cages in side-by-side relation except where a wide flat device is used to essentially replace the disc. This done for lateral stability of the vertebrae, so that the vertebrae do not pivot laterally relative to the interbody implant. Two such cylindrical cages have also been used to increase the area of bearing surfaces engaging the vertebral surfaces to thereby minimize subsidence of the cages into the vertebrae. Implanting such a pair of cylindrical cages requires that two bores be cut into the vertebral surfaces to receive the two cages.

SUMMARY OF THE INVENTION

The present invention provides an arrangement for effective use of a single interbody spacer member by center line positioning of a threaded interbody spacer or fusion cage having a winged end cap for placement between a pair of spaced apart, but adjacent vertebrae. In general, the spacer member engages inner regions of the adjacent vertebrae while the end cap engages the outer regions of the vertebrae.

The interbody spacer is a threaded spacer, including superior and inferior surfaces which have helical threads cut into the surfaces in such a manner that the outer surfaces of the threads form a partial cylindrical surface. Lateral or side surfaces of the spacer member are cylindrically concave to increase the intervertebral volume available to receive spinal fusion promoting material to fuse the adjacent vertebrae. A partial cylindrical spacer receiving bore is cut into the mutually facing surfaces of the spaced apart vertebrae along a median plane of the subject spine, through the adjacent vertebra edge regions. The spacer member is threaded into the bore, using an implant tool, to a position in which the cylindrical surfaces engage central regions of the upper and lower vertebrae.

The end cap has superior and inferior surfaces preferably shaped to conform to the natural shape of the edge regions of the adjacent vertebrae, as modified by the spacer receiving cylindrical bore formed into the surfaces of the vertebrae. The end cap has connection structure for securing the end cap to the spacer member. Preferably, such connection structure includes an opposed pair of posteriorly extending, resilient pawls which are adapted to snap into recesses formed into the side surfaces of the spacer member. The end cap preferably includes laterally extending wings or extensions which are shaped to engage segments of the edge regions of the vertebrae at positions spaced laterally of the median plane. The wings wedge between the vertebrae to prevent the vertebrae from tendencies to pivot laterally about the spacer member positioned along the median plane. The wings in conjunction with the midline spacer cooperate to prevent side to side or lateral rotation about the implant and thereby stabilize the vertebrae on either side of the spacer relative to each other.

A central cavity may be formed through the interbody spacer from one lateral surface to the other. The central cavity is intended to receive additional bone fusion material to promote fusion between the adjacent vertebrae or opposite sides of the spacer. Alternatively, other openings and apertures can be formed in the spacer. The end surfaces may be provided with threaded bores to receive an installation tool employed to implant the interbody spacer between an adjacent pair of vertebrae. The end cap may also be provided with openings, where they are structurally appropriate, to receive the bone fusion promoting material.

The threads, which extend along and form major parts of the superior and inferior surfaces of the spacer member, have inner roots and outer crests. Outer surfaces of the crests are substantially cylindrical segments, bounded by intersections with the side surfaces of the spacer member. That is, outer radii of the crests are preferably substantially constant along the axial length thereof. However, the radii of the roots of the threads generally diminish in progressing in a posterior direction to near approximately a midpoint and thereafter remain substantially constant to the posterior of the spacer member. In particular, the roots preferably diminish conically from front to back to a middle region or somewhat posterior of the exact middle. From that point to the posterior end, the radii of the roots are constant or cylindrical, resulting in an overall funnel profile shape of the thread roots and the surface of the spacer member formed by the thread roots. The purpose of the reduction in root radius near the front or anterior of the spacer member is to provide greater anterior support and thereby create or maintain a desired lordotic angle or degree of lordosis of the vertebrae.

OBJECTS AND ADVANTAGES OF THE INVENTION

Therefore, the objects of the present invention include: providing an improved arrangement for placing an implant including interbody spacer structure between an adjacent pair of vertebrae to maintain a desired spacing therebetween; providing such an interbody spacer structure formed by a single, center line mounted spacer member, that is, positioned in substantial alignment with a medial plane of the body through the spine, and an end cap member connected to and cooperating with the spacer member; providing such a centerline spacer structure in which the spacer member has substantially cylindrical surfaces and is threaded for threading into a bore formed into and between mutually facing surfaces of an adjacent pair of vertebrae; providing such an arrangement in which crests of the spacer threads are substantially equal in radius along the axial length of the spacer while roots of the threads diminish in radius from near an anterior end to near an axial midpoint to provide greater support against subsidence on the anterior side of the spacer to help support adjacent vertebrae in a desired angular or lordotic relationship; providing such a structure in which the radius of the root of the threads diminishes at a constant rate from near an anterior end toward the posterior end until near the axial midline after which the radius of the thread root becomes generally constant to provide a substantially funnel shaped profile or funnel shape to the interior body or shape of the spacer formed by the thread root; providing such a structure in which the spacer member includes cylindrically concave lateral or side surfaces that join the upper and lower abutment surfaces on opposite lateral sides of the spacer member; providing such an arrangement wherein the shape and design of the interbody spacer member provides strength while reducing volume and weight; providing such a structure in which the spacer member can be either solid or partly hollow and which is provided with openings in structurally appropriate places in order to allow packing with bone chips or other bone fusion promoting materials; providing such a structure having a spacer with a thread that has a crest of generally constant radius and a root that has a radius that reduces evenly from near an anterior end to near an axial center of the spacer and thereafter remain generally constant so that the root forms a partial funnel shaped surface; providing such a structure which minimizes surgical alteration of the vertebral bones between which a threaded cylindrical spacer is implanted; providing such a structure which requires only a single interbody spacer member positioned at a medial plane or centerline between the adjacent vertebrae; providing such an arrangement including a laterally extending stabilizing structure engaged with the spacer member and the adjacent vertebrae to prevent pivoting of the vertebrae laterally about the single interbody spacer; providing such an arrangement including an end cap which is secured to the spacer member and which engages edge regions of the mutually facing surfaces of the adjacent vertebrae; providing such an end cap including wings or extensions which extend laterally of the spacer member to engage a substantial portion of the edge regions of the adjacent vertebrae; providing such an end cap which is secured to the spacer member by connectors, especially a pair of opposed resilient pawls which extend posteriorly from the end cap to engage recesses formed on the spacer member; providing such an end cap including openings formed therethrough to receive spinal fusion promoting material; and providing such a threaded centerline interbody spacer structure with a winged end cap which is economical to manufacture, which is relatively simple to implant, which is efficient in operation, and which is particularly well suited for its intended usage.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is a fragmentary diagrammatic front elevational view of a human spine, with a pair of adjacent vertebrae separated by a spinal disc prior to installation of the present invention between the vertebrae.

FIG. 6 is a view similar to FIG. 5 and illustrates the spine subsequent to a laminectomy procedure to remove the disc, with intervertebral separating tools positioned between the vertebrae.

FIG. 7 is a view similar to FIG. 5 and illustrates the vertebrae separated by the separating tools and cylindrically bored to produce radiused upper and lower channels in the respective vertebrae to receive the interbody spacer of the present invention.

FIG. 8 is a diagrammatic plan view, taken on line 8—8 of FIG. 7, at a reduced scale and illustrates a vertebra after boring and with the separating tools in place.

FIG. 9 is a somewhat enlarged, fragmentary exploded perspective view illustrating an interbody spacer member and a spacer implanting tool assembly for use in implanting the spacer member between an adjacent pair of vertebrae.

FIG. 10 is a fragmentary plan view, at a reduced scale, of the interbody spacer member positioned between a pair of adjacent vertebrae, with the spacer implanting tool still engaged with the spacer and the vertebrae shown in phantom lines.

FIG. 11 is a fragmentary, side elevational view of the interbody spacer member positioned between the vertebrae shown in cross section, with the spacer implanting tool still engaged with the spacer.

FIG. 12 is a view similar to FIG. 10, at a somewhat enlarged scale, and illustrates the beginning of retraction of the spacer implanting tool from the spacer member with the vertebrae shown in phantom.

FIG. 13 is a fragmentary top plan view illustrating an interbody spacer member in place between a pair of vertebrae that are shown in phantom and an end cap implanting tool engaged with a winged end cap of the present invention just prior to installation of the end cap on the spacer member.

FIG. 14 is a view similar to FIG. 13 and illustrates the end cap just prior to complete engagement with the interbody spacer member.

FIG. 15 is a further fragmentary view similar to FIG. 13 and illustrates the end cap fully secured to the interbody spacer member.

FIG. 16 is an enlarged, fragmentary front elevational view of the winged end cap fully implanted and engaging edge regions of the adjacent pair of vertebrae.

FIG. 17 is a fragmentary enlarged longitudinal cross sectional view of the interbody spacer member and end cap engaged by an end cap removal tool.

DETAILED DESCRIPTION OF THE INVENTION

Figure 1:
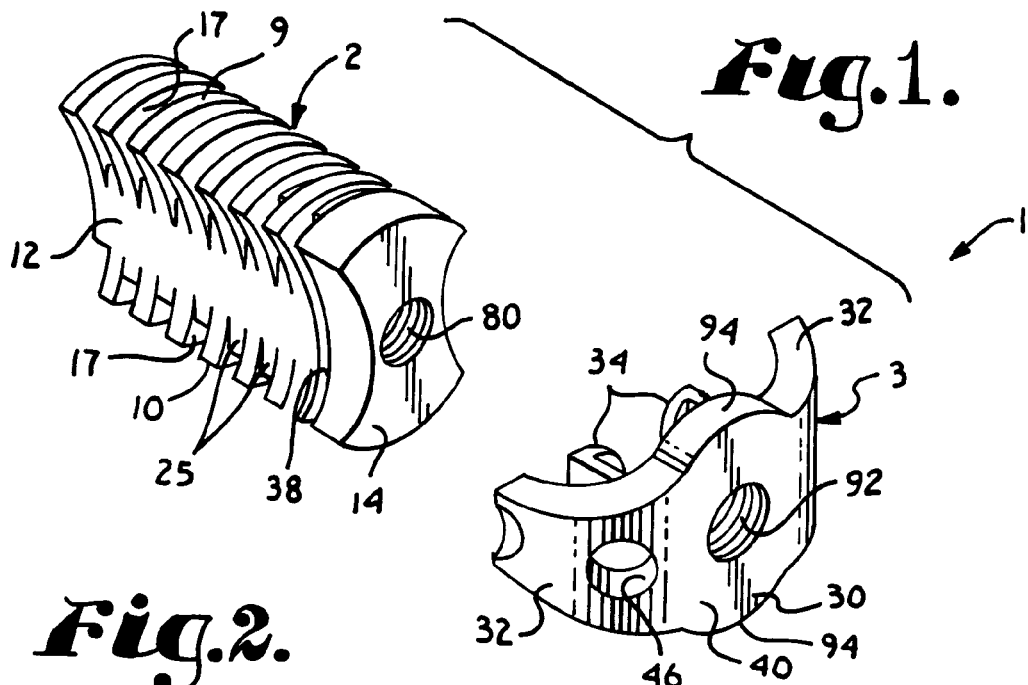
FIG. 1 is an enlarged exploded perspective view of a centerline interbody spacer member and a winged cap cooperating therewith which embody the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a threaded center line cage structure or assembly which embodies the present invention. The assembly 1 generally includes an interbody spacer member 2 and an end cap member 3 that is operably secured to the spacer member 2. The spacer member 2 and end cap 3 cooperate to maintain a beneficial spacing and mutual orientation between a pair of adjacent vertebrae 6 and 7 (FIG. 11) and to resist side to side rotation of each vertebrae 6 and 7 relative to the adjacent vertebrae 6 or 7. The assembly 1 provides a stable relationship between the vertebrae 6 and 7 with only a single spacer screw in type member 2 therebetween. By using a single spacer member 2 instead of a pair of laterally positioned spacers, an increased volume is provided between the vertebrae 6 and 7 to receive material which promotes bone fusion or osteosynthesis to thereby facilitate fusing together of the vertebrae 6 and 7.

Figure 2:
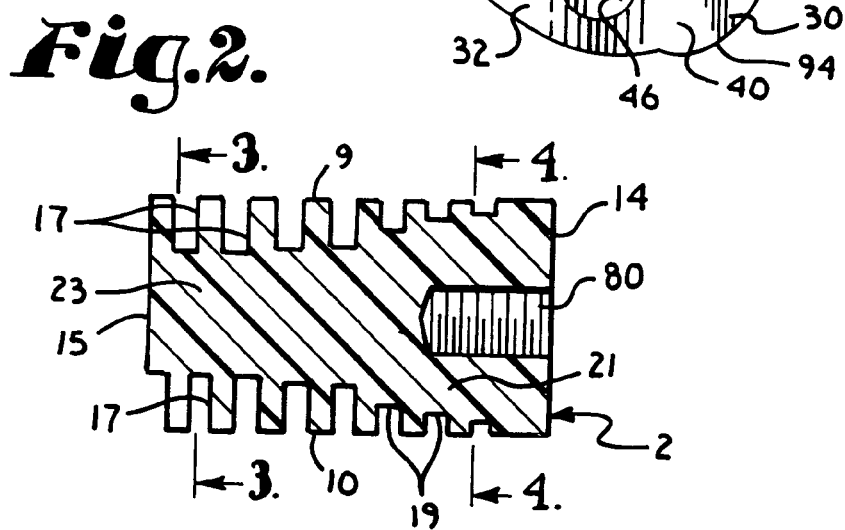
FIG. 2 is an enlarged longitudinal cross sectional view of the interbody spacer member and illustrates a diminishing radius of the thread root of the member from a front end to a middle thereof.
Figure 3:
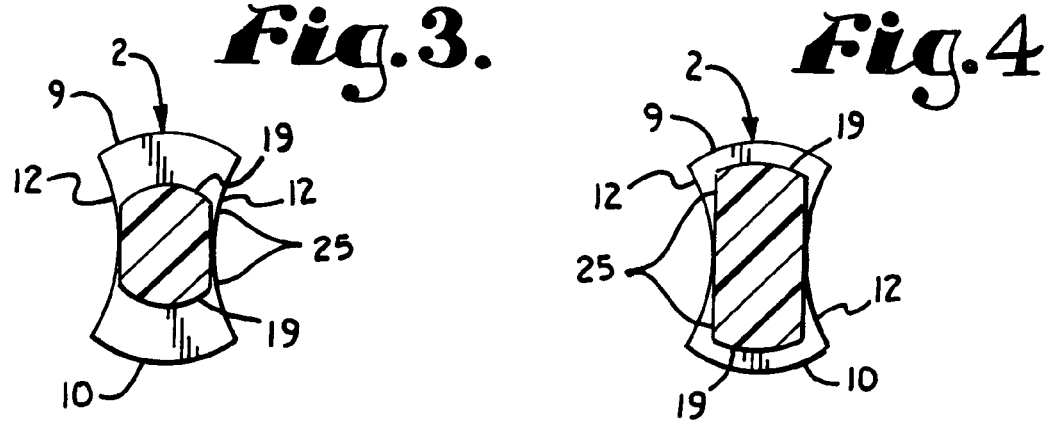
FIG. 3 is a transverse cross sectional view of the interbody spacer member, taken along line 3—3 of FIG. 2, and illustrating a root shape and size of the member near a rear end of the member.
Figure 4:
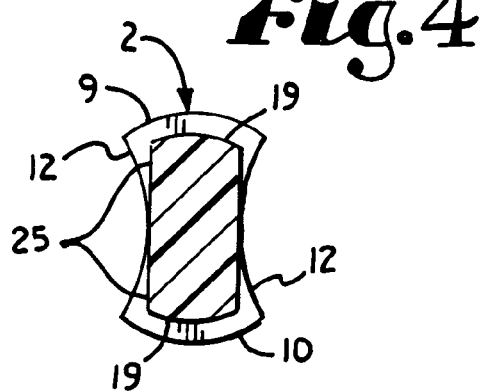
FIG. 4 is a transverse cross sectional view of the interbody spacer member, taken along line 4—4 of FIG. 2, and illustrating a root shape and size of the member near a front end of the member.

The illustrated spacer member or cage 2 has a partial convex cylindrical shaped upper and lower (superior and inferior) surfaces 9 and 10 and concave cylindrical lateral surfaces 12. Front and rear (anterior and posterior) surfaces 14 and 15 are generally planar or flat. The upper and lower surfaces 9 and 10 are formed by a helical wound thread 17 which extend along the top and bottom of the spacer member 2. The upper and lower surfaces 9 and 10 are crests of the threads 17 which are constant in radius with spaces therebetween for each turn of the thread. Roots 19 associated with each full turn of the thread 17 have radii which diminish conically from front to rear within a conical region 21 and near the axial center of the spacer member 2 become constant throughout a rearwardly located partially cylindrical shaped region 23 that has the thread 17 extending outwardly between portions of the region 23 defined by the roots 19. The cylindrical region 23 begins at the end of the conical region 21 with the shortest radius, thereby giving the roots 19 a generally "funnel" shaped profile, or side view, as illustrated in FIG. 2 and by comparison of FIGS. 3 and 4. The overall funnel shaped surface is defined by the region covered by the thread roots 19 and has discontinuous turns spaced by the thread 17 and the lateral surfaces 12.

Side areas 25 adjacent the thread roots 19 are flattened or relieved from the concave cylindrical shape of the lateral surfaces 12 to thereby increase the volume of space between the vertebrae 6 and 7 to receive material promoting fusion of the vertebrae. The flattened side areas 25 illustrated are approximately tangent to the lateral surfaces 12 of the spacer member 2. Although not shown, it is foreseen that the spacer member 2 could be provided with additional openings, such as through and joining the lateral surfaces 12, to provide additional volume between the vertebrae 6 and 7 for receiving bone fusion promoting material.

Referring to FIGS. 1 and 13–16, the end cap 3 includes a center section 30 and wing sections 32 extending laterally of the center section 30 and curving in a posterior direction therefrom. The front of the end cap 3 is preferably sized, shaped and designed to follow the contour of the front or anterior edge of the vertebrae 6 and 7. The end cap 3 includes structure for securing it to the spacer member 2. The illustrated end cap 3 includes a pair of opposed resilient pawls 34 extending from a posterior surface 36 (FIG. 13) of the end cap 3 at the center section 30. The pawls 34 are positioned to engage recesses 38 (FIGS. 1 and 14) formed into the lateral surfaces 12 of the spacer member 2 by deforming as the end cap is slid over the anterior end of the spacer member (see FIG. 14) and then resiliently returning to a gripping shape (as seen in FIG. 15) to hold the end cap 3 on the spacer number 2. Alternatively, other structure or means for securing the end cap 3 to the spacer member 2 may be employed in the assembly 1.

The illustrated wing sections 32 taper as they extend from the center section 30 and curve backward or in a posterior direction relative to the spine, such that the posterior surface 36 is concave and an opposite anterior surface 40 (FIG. 13) of the end cap 3 is convex. The curvature of the wing sections 32 is intended to conform to the curvature of an outer region 42 (FIGS. 13 and 14) of the vertebrae 6 and 7. The tapered shape of wing sections 32 is intended to generally conform to outer regions of the vertebrae 6 and 7 when they are in the desired degree of lordosis or angular relation, so that an upper and lower surface 43 engages the strongest and hardest portion of the anterior end plate of each vertebrae 6 and 7. The outer regions 42 of the vertebrae 6 and 7 surround inner regions 44 thereof. The wing sections 32 preferably include apertures 46 formed therethrough to provide for the implanting of spinal fusion promoting material between the vertebrae 6 and 7 after the assembly 1 is implanted.

The cage assembly 1 is preferably formed of a strong, light weight material which either does not react at all with the tissues and chemicals within its implanted environment or which does react therewith only in a beneficial manner. The materials may include various metallic alloys, such as stainless steels, titanium alloys, or tantalum alloys or synthetic materials or composites, such as resins, polymers, or carbon fiber reinforced polymers. It is also foreseen that the assembly 1 can be formed of a material which will be replaced by the body, over time, by boney tissue. Biological implants of this type may be constructed of bone or bone based material or certain bio-active resins. The spacer member 2 and end cap 3 may be manufactured using any of a number of known processes, such as casting or molding, machining, sintering, or combinations of such processes.

FIGS. 5–8 illustrate stages in the preparation of vertically adjacent vertebrae 6 and 7 for implanting the center line cage assembly 1 therebetween. FIG. 5 is a simplified view of the two adjacent vertebrae 6 and 7 separated by an intervertebral disc 50, with ligaments and other structures omitted for simplicity. When the disc 50 is malformed, injured, diseased, mispositioned by age or injury, or the like and does not respond to less radical treatments, it is sometimes necessary and/or beneficial to remove the disc 50, by a laminectomy procedure, and to replace the disc 50 by spacer structure which maintains the mutual spacing and angular orientation of the vertebrae 6 and 7 in a normal configuration or even produces an improved alignment so as to help correct spinal curvature problems. Often, such spacer structure is used in conjunction with techniques to fuse the vertebrae 6 and 7 into a permanently fixed relationship.

FIG. 6 illustrates the vertebrae 6 and 7 subsequent to the laminectomy and with a pair of vertebrae spreading tools 52 of a scissors type inserted between the vertebrae 6 and 7. FIG. 7 shows the vertebrae 6 and 7 spread apart a desired distance, using the tools 52, and upper and lower radiused channels 54 which have been cut partially into respective mutually facing surfaces 55 and 56 of the vertebrae 6 and 7 to receive the partly screw in spacer member 2. FIG. 8 shows the vertebra 7 with the partial cylindrical channels 54, and also illustrates the positioning of the tools 52 during the implantation procedure.

FIGS. 9–12 illustrate stages in the implantation of the spacer member 2 between the vertebrae 6 and 7, using a spacer implanting tool 60. The tool 60 has an inner rod 62 terminating in a threaded distal (to the surgeon) end 64 and a knob 66 at an opposite proximal end. The rod 62 is positioned coaxially within an outer tube 68 by a plurality of axially spaced bushings 70 (FIG. 10). The tube 68 has a pair of diametrically spaced paddles 72 at a distal end and a pair of transversely extending handles 74 at an opposite proximal end. The paddles 72 have external threads 76 which have the same radius and are compatible with the threads 17 of the spacer member 2. Additionally, the paddles 72 have inner convex surfaces 78 which are cylindrical with the same cylindrical radius as the concave lateral surfaces 12 of the spacer member 2.

The spacer implanting tool 60 is used to implant the spacer member 2 between the vertebrae 6 and 7 within the center line channels 54 which have been previously cut into the vertebrae 6 and 7, while at a desired spacing. The tool 60 is engaged with the spacer member 2 with the paddles 72 on opposite sides, such that the inner cylindrical surfaces 78 snugly engage the lateral cylindrical surfaces 12 of the spacer member 2. The paddle threads 76 are formed in such a manner that when the paddles 72 are properly positioned axially with respect to the spacer member 2, the paddle threads 76 form a continuous helical thread with the threads 17 on the upper and lower surfaces 9 and 10 of the spacer member 2. With the paddles 72 thus positioned relative to the spacer member 2, the threaded end 64 of the rod 62 is threaded into a threaded bore or socket 80 (FIG. 1) formed into the front surface 14 of the spacer member 2 and tightened using the knob 66.

When the tool 60 has been secured to the spacer member 2, the spacer member 2 is threaded or screwed into the spaced vertebral channels 54. As the spacer member 2 and paddles 72 are threaded between the vertebrae 6 and 7, the threads 17 and 76 tap a thread into the channels 54. Threading continues until the spacer member 2 is properly positioned relative to the vertebrae 6 and 7 to engage the inner or central regions 44 thereof. Rotation of the spacer member 2 is stopped when in an upright orientations (FIGS. 10 and 11) so that the upper and lower surfaces 9 and 10 thereof respectively engage the upper and lower vertebrae 6 and 7.

To remove the spacer implanting tool 60 from the spacer member 2, once it is implanted in a desired position and orientation, the outer tube 68 is translated in a proximal direction relative to the inner rod 62, leaving only a portion of the paddles 72 engaging the lateral surfaces 12 of the spacer member 2 (FIG. 12). The tube 68 is then held, using the handles 74, while the rod 62 is rotated, using the knob 66, to unthread the end 64 thereof from the bore 80 in the front end 14 of the spacer member 2. Afterwards, the paddles 72 are fully withdrawn from the lateral surfaces or sides 12 of the spacer member 2.

FIGS. 13–15 illustrate stages in the connection of the end cap 3 to the previously implanted spacer member 2. FIG. 13 illustrates an exemplary end cap implanting tool 85 which may be used for this purpose. The tool 85 has a shaft 86 with a pair of handles 87 at a proximal end and a threaded distal end 88 joined to the shaft 86 at a shoulder 89. The threaded end is sized to fit into the threaded bore 80 of the spacer member 2. The threaded end 88 is inserted through a threaded bore 92 formed through the center section 30 of the end cap 3 and threadedly engaged with the threaded bore 80 in the spacer member 2. The shaft 86 is rotated, using the handles 87, to thread the end 88 further into the bore 80, thereby urging the shoulder 89 against the anterior surface 40 of the center section 30. By this means, the pawls 34 are urged past the front surface 14 of the spacer member 2 and into the pawl receiving recesses or grooves 38 formed into the lateral surfaces 12 of the spacer member 2. When that occurs, the center section 30 and wing sections 32 of the end cap 3 are generally aligned with the outer regions 42 of the vertebrae 6 and 7, for engagement thereby. The center section 30 preferably has upper and lower edge surfaces 94 which are cylindrical in shape and of the same diameter as the center line channels 54 for close engagement and support of the center section with the vertebrae 6 and 7 at the outer regions 42 (see FIG. 16) at the channels 54.

Although the end cap 3 will typically be permanently left attached to the spacer member 2, under some circumstances, it may be necessary to detach the end cap 3 therefrom. FIG. 17 illustrates an end cap removal tool 96 which may be used for such a purpose. The tool 96 has a shaft 97 terminating in a threaded distal end 98 with an abutment surface 99 at an ultimate end. The threaded end 98 is sized and threaded to fit into the threaded bore 92 in the center section 30 of the end cap 3 and is too large to fit into the threaded bore 80 of the spacer member 2. When it is necessary to detach an end cap 3 from an implanted spacer member 2, the threaded end 98 is threaded into the bore 92 until the abutment surface 99 engages the front surface 14 of the spacer member 2. Rotation of the shaft 97 continues, using a handle (not shown) thereon, to urge the end cap 3 anteriorly away from the spacer member 2, thereby deforming and retracting the pawls 34 from the recesses 38 in the side surfaces 12 of the spacer member 2. Rotation may be continued until the pawls 34 clear past the front surface 14 of the spacer member 2 and the end cap 3 is then pulled from the spacer member 2.

The cage assembly 1 of the present invention enables the use of a single spacer member or cage 2 positioned along a "center line" of the vertebrae 6 and 7, that is, within a median plane 102 (FIG. 13) of the body incorporating the vertebrae 6 and 7. The spacer member 2 engages inner regions 44 of the mutually facing vertebral surfaces 55 and 56 of the vertebrae 6 and 7. The end cap 3 engages outer regions 42 of the vertebrae 6 and 7 and, thereby, cooperates with the spacer member 2 to provide lateral stability to the vertebrae 6 and 7 with the spacer member 2 implanted therebetween and located on the center line 102. Additionally, the funnel shaped profile of the roots 19 of the thread 17 of the spacer member 2 promotes a favorable angular or lordotic relationship between the vertebrae 6 and 7 (FIG. 11).

It is to be understood that while certain forms of the present invention have been illustrated and described herein, it is not to be limited to the specific forms or arrangement of parts described and shown.

What is claimed and desired to be secured by Letters Patent is as follows:

1. A spinal fusion interbody spacer assembly for maintaining a selected intervertebral spacing between an adjacent pair of vertebrae having mutually facing vertebral surfaces, each vertebral surface including an inner central region and an outer edge region, said assembly comprising:
   (a) an interbody spacer member sized and shaped so as to be adapted to enable implanting of said member between and in touching relationship at both a top and bottom of the spacer respectively with an adjacent pair of vertebrae to engage and support the central regions of mutually facing vertebral surfaces of the vertebrae; said spacer member having a longitudinal axis; said spacer member having front and rear ends on opposite ends of said longitudinal axis;
   (b) an end cap joinable with said spacer member at said front end and configured in such a manner as to be adapted to enable implanting between facing vertebrae so as to resist subsidence of the vertebrae about the assembly, said end cap including a pair of wing portions extending laterally on opposite sides of said end cap; said wing portions having an arcuate curvature and convex outer surfaces; the wing portions being sized and shaped so as to have upper and lower wing surfaces; each wing surface being configured to engage and support an anterior edge from a center to lateral sides of respective facing vertebral surfaces; and
   (c) said end cap being removably securable to said spacer member and cooperating therewith to maintain the selected intervertebral spacing between the vertebrae.

2. An assembly as set forth in claim 1 wherein:
   (a) said spacer member and said end cap cooperate to position said spacer member in substantial alignment with a median plane of the vertebrae.

3. An assembly as set forth in claim 1 and including:
   (a) said end cap and said wing portions having a generally continuous superior cap surface and an opposite inferior cap surface; and
   (b) said end cap being secured to said spacer member in such a manner that when in use said cap surfaces are adapted to engage the edge regions of the vertebral surfaces.

4. A method of stabilizing a pair of vertebrae including the steps of:
   (a) placing a single midline spacer having a cylindrical profile between said vertebrae so as to located said spacer in a median plane relative to said vertebrae and such that a top and a bottom of the spacer are in touching relationship with mutually facing surfaces of respective vertebrae; said spacer having a longitudinal axis with front and rear ends located along said longitudinal axis; and
   (b) placing an end cap on said front end of said spacer wherein said end cap includes wings having convex outer surfaces; the wings extending laterally outward and sized and shaped to conform to the anterior curvature of the vertebrae along the entire anterior edges to the lateral sides thereof; the wings being sized and shaped to be positioned between the vertebrae so that superior and inferior surfaces of the wings engage respective facing surfaces of the vertebrae while following the anterior curvature of respective vertebrae; such that said end cap engages said vertebrae and resists lateral rotation of said vertebrae about said spacer and subsidence of the vertebrae relative to said spacer.

5. A centerline spinal fusion interbody spacer assembly for implanting to maintain a selected intervertebral spacing between an adjacent pair of vertebrae having mutually facing vertebral surfaces, each vertebra having an inner central region and an outer edge region with lateral sides, said assembly comprising:
   (a) an interbody spacer member configured, sized, and shaped to enable implanting between an adjacent pair of vertebrae so as to touchingly engage mutually facing vertebral surfaces of the vertebrae with respective top and bottom surfaces of said spacer member to thereby maintain a selected intervertebral spacing therebetween;
   (b) said spacer member being further configured to enable said spacer member to be positioned in substantial alignment with a median plane of the vertebrae as a single such spacer; said spacer member having front and rear ends; and
   (c) an end cap member securable to said spacer member front end so as to extend in front of said spacer member and having a superior cap surface and an opposite inferior cap surface; said superior and inferior cap surfaces being sized and shaped to be positioned between said vertebrae and configured to engage respective facing vertebral surfaces of said vertebrae while following the anterior curvature of a respective vertebra; said end cap member including a pair of wing portions; each wing portion having a convex outer surface and being sized and shaped so as to substantially conform to the shape of the anterior edges of the vertebrae from a center to the lateral sides of the vertebrae; the end cap and wing portions being configured to support the entire anterior edges of facing vertebral surfaces of adjacent vertebrae.

6. In a spinal fusion assembly having a centerline interbody spacer; said spacer being sized and shaped to be positioned between facing surfaces of adjacent vertebrae such that top and bottom surfaces of said spacer are in touching relationship with facing surfaces of respective vertebrae and including an end cap, said spacer member having front and rear ends with the end cap being joined to the front end of the spacer, the improvement comprising:

(a) said end cap including a pair of laterally extending wings having inferior and superior surfaces the wings being sized and shaped so as to conform to the anterior curvature of the edge of a respective vertebra such that the superior and inferior surfaces of the wings are configured to engage respective vertebra from whereat the cap joins to the spacer to the lateral sides of said vertebrae so as to resist subsidence of the vertebrae with respect to said assembly; the end cap and wings being configured to support the entire anterior edges of facing vertebral surfaces of adjacent vertebrae.

7. A centerline spinal fusion interbody spacer assembly for implanting to maintain a selected intervertebral spacing between an adjacent pair of vertebrae having mutually facing vertebral surfaces, each vertebra having an inner central region and an outer edge region with lateral sides, said assembly comprising:

(a) an interbody spacer member configured sized and shaped to enable implanting between an adjacent pair of vertebrae to engage mutually facing vertebral surfaces of the vertebrae to thereby maintain a selected intervertebral spacing therebetween;

(b) said spacer member being further configured to enable said spacer member to be positioned in substantial alignment with a median plane of the vertebrae as a single such spacer;

(c) said spacer member being a screw in type spacer and including an external thread positioned on said spacer member so that the spacer threadedly engages the vertebral surfaces when implanted between the vertebrae; and (d) an end cap member securable to said spacer member having a superior cap surface and an opposite inferior cap surface; said superior and inferior cap surfaces being sized and configured to shaped to be positioned between said vertebrae and configured to engage respective facing vertebral surfaces of said vertebrae while following the anterior curvature of a respective vertebra; said end cap member including a pair of wing portions; each wing portion having a convex outer surface and being sized and shaped so as to substantially conform to the shape of the anterior edges of the vertebrae from the median plane to the lateral sides of the vertebrae; the end cap member and wing portions being configured to support entire anterior edges of facing vertebral surfaces of adjacent vertebrae.

8. A centerline spinal fusion interbody spacer assembly for implanting to maintain a selected intervertebral spacing between an adjacent pair of vertebrae having mutually facing vertebral surfaces, each vertebra having an inner central region and an outer edge region with lateral sides, said assembly comprising:

(a) an interbody spacer member configured, sized and shaped to enable implanting between an adjacent pair of vertebrae to engage mutually facing vertebral surfaces of the vertebrae to thereby maintain a selected intervertebral spacing therebetween;

(b) said spacer member being further configured to enable said spacer member to be positioned in substantial alignment with a median plane of the vertebrae as a single such spacer;

(c) said spacer member including a superior vertebra engaging surface and an opposite inferior vertebra engaging surface;

(d) at least a portion of each said superior vertebra engaging surface and said inferior vertebra engaging surface have a thread thereon, said thread having crests that are aligned to form a partial cylindrical surface; and (e) an end cap member securable to said spacer member having a superior cap surface and an opposite inferior cap surface; said superior and inferior cap surfaces being sized and shaped to be positioned between said vertebrae and engage respective facing vertebral surfaces of said vertebrae while following the anterior curvature of a respective vertebra; said end cap member including a pair of wing portions; each wing portion having a convex outer surface and being sized and shaped so as to substantially conform to the shape of the anterior edges of the vertebrae from the median plane to the lateral sides of the vertebrae; the end cap member and wing portions being configured to support entire anterior edges of facing vertebral surfaces of adjacent vertebrae.

9. An assembly as set forth in claim 8 wherein said spacer member includes:

(a) opposite lateral surfaces; and (b) each of said lateral surfaces are substantially concave.

10. An assembly as set forth in claim 8 wherein:

(a) said thread has a root that follows a path located on a funnel shaped and discontinuous surface, the surface having a greatest radius near an anterior end of said spacer member and a smallest radius near a posterior end of said spacer member.

11. A spinal fusion interbody spacer assembly for maintaining a selected intervertebral spacing between an adjacent pair of vertebrae having mutually facing vertebral surfaces, each vertebral surface including an inner central region and an outer edge region, said assembly comprising:

(a) an interbody spacer member sized and shaped so as to be adapted to enable implanting of said member between an adjacent pair of vertebrae to engage and support central regions of mutually facing vertebral surfaces of the vertebrae;

(b) an end cap joinable with said spacer member and configured in such a manner as to be adapted to enable implanting between facing edge regions of the vertebrae so as to resist subsidence of the vertebrae about the assembly, said end cap including a pair of wing portions extending laterally on opposite sides of said end cap; said wing portions having an arcuate curvature and convex outer surfaces; the end cap and wing portions being configured to support entire anterior edges of facing vertebral surfaces of adjacent vertebrae;

(c) said end cap being removably securable to said spacer member and cooperating therewith to maintain the selected intervertebral spacing between the vertebrae;

(d) at least one resilient pawl positioned on said end cap;

(e) a pawl receiving recess formed on said spacer member; and (f) said end cap being secured to said spacer member by resilient engagement of said pawl with said recess.

12. A spinal fusion interbody spacer assembly for maintaining a selected intervertebral spacing between an adjacent pair of vertebrae having mutually facing vertebral surfaces, each vertebral surface including an inner central region and an outer edge region, said assembly comprising:

(a) an interbody spacer member sized and shaped so as to be adapted to enable implanting of said member between an adjacent pair of vertebrae to engage and support central regions of mutually facing vertebral surfaces of the vertebrae;

(b) an end cap joinable with said spacer member and configured in such a manner as to be adapted to enable implanting between facing edge regions of the vertebrae so as to resist subsidence of the vertebrae about the assembly, said end cap including a pair of wing portions extending laterally on opposite sides of said end cap; said wing portions having an arcuate curvature and convex outer surfaces; the end cap and wing portions being configured to support entire anterior edges of facing vertebral surfaces of adjacent vertebrae;

(c) said end cap being removably securable to said spacer member and cooperating therewith to maintain the selected intervertebral spacing between the vertebrae;

(d) a pair of resilient pawls positioned in opposed relation on said end cap;

(e) a recess structure forming a respective pawl receiving recess on each of opposite sides of said spacer member; and (f) said end cap being secured to said spacer member by resilient engagement of each of said pawls with a respective pawl receiving recess of said spacer member.

13. A spinal fusion interbody spacer assembly for maintaining a selected intervertebral spacing between an adjacent pair of vertebrae having mutually facing vertebral surfaces, each vertebral surface including an inner central region and an outer edge region, said assembly comprising:

(a) an interbody spacer member sized and shaped so as to be adapted to enable implanting of said member between an adjacent pair of vertebrae to engage and support central regions of mutually facing vertebral surfaces of the vertebrae;

(b) said spacer member including external threads positioned on said spacer member in such a manner as to threadedly engage the vertebral surfaces when implanted between the vertebrae;

(c) an end cap joinable with said spacer member and configured in such a manner as to be adapted to enable implanting between facing edge regions of the vertebrae so as to resist subsidence of the vertebrae about the assembly, said end cap including a pair of wing portions extending laterally on opposite sides of said end cap; said wing portions having an arcuate curvature and convex outer surfaces; the end cap and wing portions being configured to support entire anterior edges of facing vertebral surfaces of adjacent vertebrae; and (d) said end cap being removably securable to said spacer member and cooperating therewith to maintain the selected intervertebral spacing between the vertebrae.

14. An assembly as set forth in claim 13 wherein said spacer member includes:

(a) a superior vertebra engaging surface and an opposite inferior vertebra engaging surface; and (b) at least a portion of each of said superior surface and said inferior surface having threads thereon with crests that are located so as to be positioned on a cylindrical shaped and discontinuous surface.

15. An assembly as set forth in claim 14 wherein said spacer member includes:

(a) opposite lateral surfaces; and (b) each of said lateral surfaces being substantially concave.

16. An assembly as set forth in claim 14 wherein:

(a) said threads have roots that are located so as to be positioned on a funnel shaped and discontinuous surface having a greatest radius near an anterior end of said spacer member.

* * * * *